(12) United States Patent
Ho et al.

(10) Patent No.: US 12,239,679 B1
(45) Date of Patent: Mar. 4, 2025

(54) ANTIBACTERIAL MODIFIED CHITOSAN-BASED HEMOSTATIC MATERIAL AND METHOD OF MANUFACTURING THE SAME

(71) Applicant: Vien Anh Xuan Ho, Ho Chi Minh (VN)

(72) Inventors: Vien Anh Xuan Ho, Ho Chi Minh (VN); Anh Dang Tran, Ho Chi Minh (VN); Huy Vu Thanh Nguyen, Ho Chi Minh (VN)

(73) Assignees: Vien Anh Xuan Ho, Ho Chi Minh (VN); Anh Dang Tran, Ho Chi Minh (VN)

( * ) Notice: Subject to any disclaimer, the term of this patent is extended or adjusted under 35 U.S.C. 154(b) by 0 days.

(21) Appl. No.: 18/907,606

(22) Filed: Oct. 7, 2024

Related U.S. Application Data

(63) Continuation of application No. 18/818,636, filed on Aug. 29, 2024, now Pat. No. 12,188,071, and a continuation of application No. 18/592,551, filed on Mar. 1, 2024, now Pat. No. 12,042,521.

(51) Int. Cl.
| | | |
|---|---|---|
| A61K 36/07 | (2006.01) |
| A61K 8/06 | (2006.01) |
| A61K 8/9728 | (2017.01) |
| A61K 47/36 | (2006.01) |
| A61Q 19/00 | (2006.01) |
| C12N 1/20 | (2006.01) |
| C12R 1/07 | (2006.01) |
| C12R 1/23 | (2006.01) |
| C12R 1/25 | (2006.01) |

(52) U.S. Cl.
CPC .............. *A61K 36/07* (2013.01); *A61K 8/06* (2013.01); *A61K 8/9728* (2017.08); *A61K 47/36* (2013.01); *A61Q 19/00* (2013.01); *C12N 1/205* (2021.05); *A61K 2236/17* (2013.01); *A61K 2236/19* (2013.01); *A61K 2236/331* (2013.01); *A61K 2236/37* (2013.01); *A61K 2236/53* (2013.01); *C12R 2001/07* (2021.05); *C12R 2001/23* (2021.05); *C12R 2001/25* (2021.05)

(58) Field of Classification Search
None
See application file for complete search history.

*Primary Examiner* — Russell G Fiebig

(57) ABSTRACT

A method of manufacturing the antibacterial modified chitosan-based hemostatic material comprising: (i) preparing materials including: a modified chitosan ingredient and third different solutions including a solution containing polysaccharide, a solution containing dissolving solvent, and a solution containing nano silver; (ii) mixing the solutions prepared in step (i) to create a foundation mixture; (iii) loading the foundation mixture into a electrospinning device according to predetermined specifications to obtain the antibacterial modified chitosan-based hemostatic material in the form of nanofibers; and (iv) applying the antibacterial modified chitosan-based hemostatic material to a bleeding tissue on the surface of skin of a subject in need thereof to prevent bleeding and fluid exudation from the tissue, and promoting bacteriostatic and anti-inflammatory effects on the wound surface.

14 Claims, 2 Drawing Sheets

ANTIBACTERIAL MODIFIED CHITOSAN-BASED HEMOSTATIC MATERIAL AND METHOD OF MANUFACTURING THE SAME

CROSS-REFERENCE TO RELATED APPLICATIONS

This application is a continuation application of application Ser. No. 18/592,551, entitled "A method for producing a complex composition of turkey tail mushroom extract—chitosan", filed on Mar. 1, 2024, which is a continuation application of application Ser. No. 18/818,636, entitled "A chitosan composition and method of manufacturing the same", filed on Aug. 29, 2024. The patent applications identified above are incorporated here by reference in its entirety to provide continuity of disclosure.

FIELD OF THE INVENTION

The invention belongs to the field of functional polymer materials and medical technology, and particularly relates to an antibacterial modified chitosan-based hemostatic material and method of manufacturing the same and application thereof.

BACKGROUND ART

Traumatic blood loss in emergencies is the primary problem faced by emergency rescue. Fast and timely hemostasis can greatly reduce patient mortality. Therefore, it is necessary to develop an ideal hemostatic material with excellent performance and easy use. Some commonly used hemostatic materials currently include chitosan, alginate, gelatin, collagen, etc. Chitosan is one of the most commonly used hemostatic materials. It is non-toxic, harmless, biocompatible, and has a wide range of sources. Chitosan Sugar and its modified derivatives also have excellent hemostatic properties. There are many hemostatic products on the market, such as hemostatic gel, hemostatic sponge, hemostatic fiber, hemostatic gauze, etc., which have broad prospects in the field of hemostatic medical treatment in the future. prospect. However, it also has some shortcomings. Due to the varying shapes of wounds, fixed-shaped hemostatic dressings cannot completely wrap the wound in some specific situations, and thus cannot function well.

Faced with the above problems, many scholars have carried out research. For example, patent CN111375085A discloses a fluid hemostatic glue and its preparation method, and patent CN115300664A is a layered spray-on hemostatic film of chitosan and sodium polyphosphate loaded with tissue factor nanoparticles, which is mainly used for intraoperative or postoperative wounds. Hemostatic treatment. Although these products have made new breakthroughs in dealing with complex wounds, they must also be considered to prevent further deterioration of the wound caused by infection during the treatment process. They can effectively stop bleeding and be antibacterial at the same time, which will greatly reduce the pressure of emergency treatment. This brings hope for more lives. Therefore, it is necessary to develop a material that can cope with complex bleeding environments, has no skin irritation, and can quickly stop bleeding with antibacterial properties.

Therefore, in order to solve the technical problems existing in the prior art, the present invention provides an antibacterial modified chitosan-based hemostatic material and a preparation method thereof, which has good rapid hemostasis and antibacterial effects, has no toxic side effects on the human body, has low cytotoxicity, and has high biocompatibility, which is beneficial to the rapid healing of wounds. At the same time, the hemostatic and antibacterial ingredients contained in the hemostatic material have good long-term stability, which can effectively avoid the loss and failure problems in the long-term storage process; further, it can quickly stop bleeding while reducing the amount of blood absorbed, and the problem of excessive blood loss.

This invention provides solutions to achieve the above goals.

SUMMARY OF THE INVENTION

Accordingly, an objective of the present invention is to provide a method of manufacturing the antibacterial modified chitosan-based hemostatic material comprising steps performed in the following specific order:
(i) preparing materials including: a modified chitosan ingredient and third different solutions including a solution containing polysaccharide, a solution containing dissolving solvent, and a solution containing nano silver;
(ii) mixing the solutions prepared in step (i) to create a foundation mixture;
(iii) loading the foundation mixture into a electrospinning device according to predetermined specifications to obtain the antibacterial modified chitosan-based hemostatic material in the form of nanofibers; and
(iv) applying the antibacterial modified chitosan-based hemostatic material to a bleeding tissue on the surface of skin of a subject in need thereof to prevent bleeding and fluid exudation from the tissue, and promoting bacteriostatic and anti-inflammatory effects on the wound surface.

Another objective of the present invention is to provide the modified chitosan ingredient is obtained by performing steps (A) to (C):
(A) creating a chitin mixture by homogenously mixing 10 parts of a chitin ingredient from molting shell of shrimp with 1 part of a chitin ingredient from oyster mushroom; wherein the chitin mixture has a pH of 6.8-7.2;
(B) centrifuging the chitin mixture at a speed of 3500-6500 rpm to separate the residue to obtain a temporary solution; and
(C) adding (0.001-0.2) parts of Lactic anhydride into the temporary solution by dropped, adding (0.001-0.8) parts of pyridine solution combined with stirring at 50 rpm for 35 minutes, and adding (0.01-2.5) parts of ethanol solution 75% combined with stirring at 50 rpm for 5 minutes, then stop stirring and let stand for 30 minutes to obtain the modified chitosan ingredient.

Yet another objective of the present invention is to provide the solution containing polysaccharide obtained by mixing a Polysaccharopeptide (PSP) component is extracted from a solution of turkey tail mushroom extract with a first percentage (%) by weight and a Polysaccharide K (PSK) component is extracted from the solution of turkey tail mushroom extract with a second percentage (%) by weight, combining stirring for 10 minutes;
wherein the solution of turkey tail mushroom extract comprising performing in a specific order from (A') to (D'):
(A') fermenting a turkey tail mushroom mixture with the addition of a microorganism preparations in ratio (45-55): 1 at 30° C.-35° C. combined with stirring at 120 rpm for 35-40 hours, and centrifuging at a speed of 6000 rpm for 60 minutes to obtain a first solution and a first residue;
wherein the turkey tail mushroom mixture comprising (1-2) parts a first turkey tail mushroom component with (1-2) parts a second turkey tail mushroom component, (1-2) parts a third turkey tail mushroom component, (1-2) parts a fourth turkey tail mushroom component, and (1-2) parts a fifth turkey tail mushroom component;
the first turkey tail mushroom component is obtained by cultivating *Trametes versicolor* (L.) Pilat on biomass growth medium;
the second turkey tail mushroom component is obtained by cultivating *Trametes versicolor* (L.) Lioud (1920) on biomass growth medium;
the third turkey tail mushroom component is obtained by cultivating *Trametes sanguinea* (L.) Imazeki on biomass growth medium;
the fourth turkey tail mushroom component is obtained by cultivating *Trametes versicolor* BRG04 on biomass growth medium;
the fifth turkey tail mushroom component is obtained by cultivating Pycnoporus *sanguineus* (L.: Fr.) Murrill on biomass growth medium;
the biomass growth medium comprising: glucose having 30 g/L, peptone having 4 g/L, magnesium sulfate ($MgSO_4$) having 0.5 g/L, and potassium dihydrogen phosphate ($KH_2PO_4$) having 1 g/L;
wherein the microorganism preparations comprising (1-3) parts a first nutrient broth solution with (1-3) parts a second nutrient broth solution, and (1-3) parts a third nutrient broth solution;
the first nutrient broth solution cultivating *Lactobacillus plantarum* (identified on the gene bank as JQ937330.1) on LB medium;
the second nutrient broth solution cultivating *Lactobacillus acidophilus* (identified on the gene bank as OK398226.1) on LB medium; and
the third nutrient broth solution cultivating *Bacillus subtilis* (identified on the gene bank as KY777343.1) on LB medium;
(B') extracting the first residue with water at a ratio of 1:(5-7) at 100° C. for 10-15 minutes to obtain a second solution and a second residue;
(C') extracting the first residue with water at a ratio of 1:(5-7) at 55° C. for 2 hours, then filtering to remove residue, and neutralizing pH to 6.8-7.2 to obtain a third solution; and
(D') mixing the first solution with the second solution, and the third solution to obtain the solution of turkey tail mushroom extract;
wherein the polysaccharopeptide (PSP) component is extracted from the solution of turkey tail mushroom extract comprising performing in a specific order from (a) to (b):
(a) mixing the solution of turkey tail mushroom extract with water at a ratio of 1/32 with stirring at 1000 rpm for 5 minutes, then extracting at 121° C. for 35 minutes, then adding ammonium salt saturated sulfate 80% into said extract at ratio of 1:3 and overnight at 4° C. to form precipitate, and centrifuging at a speed of 8000 rpm for 15 minutes to collect a first precipitate; and
(b) dissolving the first precipitate with water at a ratio of 1:5, then filtering by the membrane filter having a pore size of 30 Kda to collect a fraction that does not pass through the membrane filter, and drying the fraction at 35° C.-42° C. for 35 hours to obtain the polysaccharopeptide (PSP) component;
wherein prepare the Polysaccharide K (PSK) component from the turkey tail mushroom extract ingredient comprising performing in a specific order from (a') to (b'):
(a') mixing the turkey tail mushroom extract ingredient with water at a ratio of 1/32 with stirring at 1000 rpm for 5 minutes, then extracting at 121° C. for 45 minutes, then adding ethanol solution 60% into said extract at ratio of 1:3 and overnight at 4° C. to form precipitate, and centrifuging at a speed of 8000 rpm for 25 minutes to collect a second precipitate; and
(b') washing the second precipitate by ethanol solution 60%, then drying at 35° C.-42° C. for 28 hours to obtain the Polysaccharide K (PSK) component.

In view of the foregoing, another objective of the present invention is to provide the solution containing nano silver obtained by performing a blend of a solution extracted from plants with a seventh percentage (%) by weight, an aqueous soluble silver salt with a eighth percentage (%) by weight, then treating by ultrasonic with amplitude 25% at 35° C.-42° C. for 10 minutes, and adding an alginate solution 1% with a ninth percentage (%) by weight, and an ascorbic acid solution with a tenth percentage (%) by weight, combined with stirring at 55° C.-60° C. for 20 minutes;
wherein the solution extracted from plants is prepared by sequentially mixing in a container a lotus leaf extract/essential oil, of a grapefruit peels extract/essential oil, a piper seeds extract/essential oil, an *ardisia* leaf extract/essential oil, a *Gomphrena celosioides* Mart. extract/essential oil to form a mixture, and a *Selaginella tamariscina* (Beauv.) Spring extract/essential oil; wherein after each addition of an extract/essential oil the mixture is stirred until the mixture is homogenous;
wherein the piper seeds extract/essential oil is extracted from piper seeds crushed or not crushed, and immersed in solvent, or saturated brine solution; in which piper seeds including *Piper nigrum* L., *Piper bavinum* C. DC., *Piper saxicola* C. DC., *Piper gymnostachyum* C. DC., *Piper brevicaule* C. DC., *Piper pierrei* C. DC, *Piper boehmeriifolium* (Miq.) Wall. ex C. DC., and *Piper retrofractum* Vahl;
wherein the *ardisia* leaf extract/essential oil is extracted from *ardisia* leaf crushed/chopped/or not chopped, and immersed in solvent, or saturated brine solution; in which *ardisia* leaf including *Ardisia balansana* Yang, *Ardisia caudata* Hemsl., *Ardisia incarnata* Pitard, *Ardisia insularis* Mez., *Ardisia maculosa* Mer., *Ardisia primulifolia* Gardn., *Ardisia pseudocrispa* Pit., *Ardisia splendens* Pit., and *Ardisia tsangii* E. Walker;
wherein the aqueous soluble silver salt is selected from the group consisting of silver acetate, silver fluogallate, silver nitrate, and silver sulfate; in which aqueous soluble silver salt has a concentration of 0.02 M.

Finally, the purpose of the invention is to provide an antibacterial modified chitosan-based hemostatic material including a first formula, a second formula, a third formula, and a fourth formula; and in which the third formula is stronger than the first formula, the second formula is stronger than the fourth formula and the first formula is stronger than the second formula; in which the comparative factor is rapid hemostasis, and antibacterial activities depend on the percentage (%) of the weight of each mixing ingredient.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

DETAILED DESCRIPTION OF THE INVENTION

Figure 1:
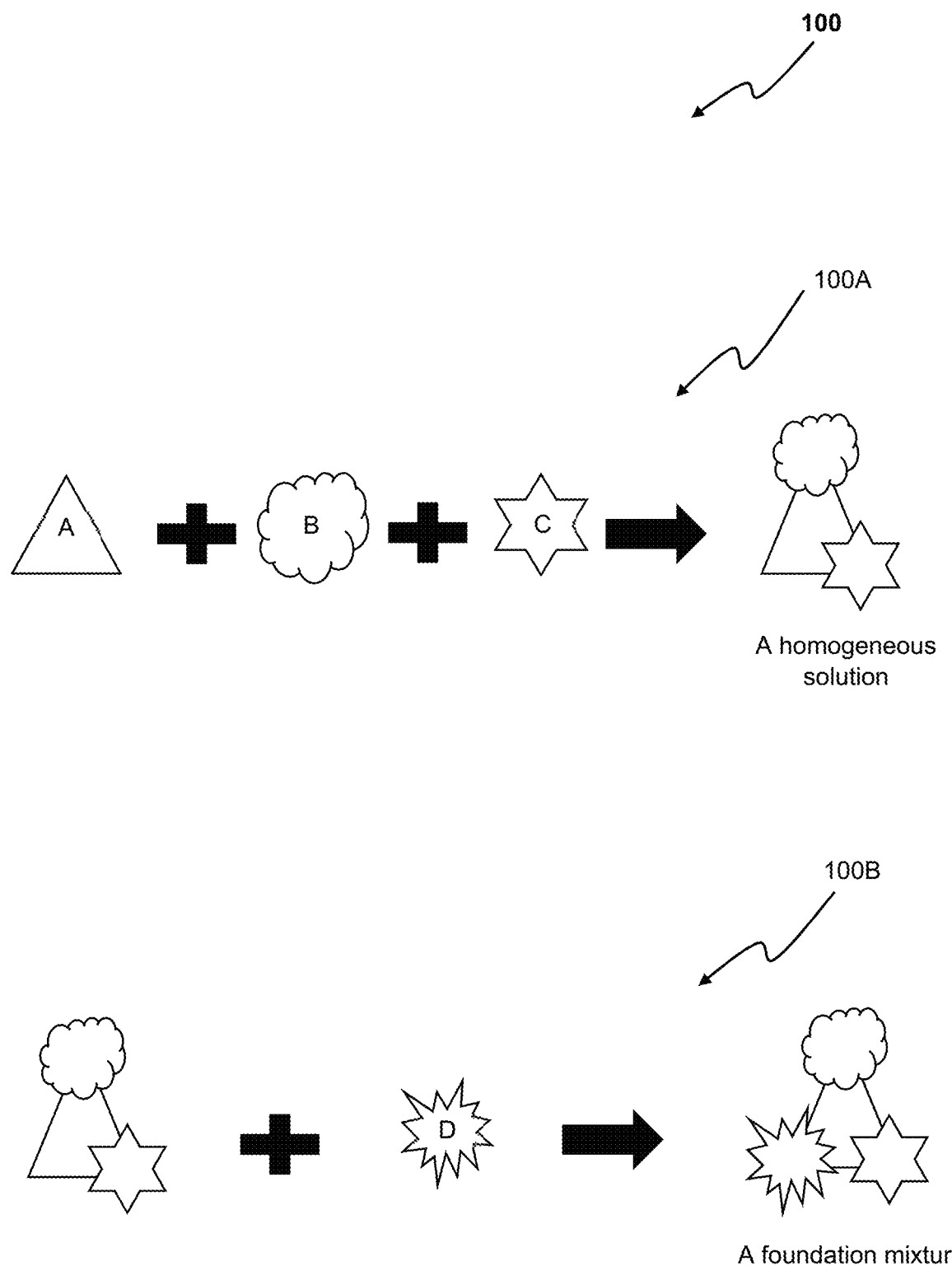
FIG. 1 is a conceptual block diagram illustrating the principle of making the antibacterial modified chitosan-based hemostatic material with an exemplary embodiment of the present invention.

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims.

Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

The present invention provides an antibacterial modified chitosan-based hemostatic material with the biocompatible properties of hemostasis, adhesion prevention, tissue healing, absorbable tissue sealing and tissue bonding. More specifically, the antibacterial modified chitosan-based hemostatic material which is rapidly degraded by humans and animals when applied directly to the wound surface of humans and mammals, including a bleeding or exudating wound surface, is able to stop bleeding, prevent adhesions, promote tissue healing, seal wounded tissue, prevent bleeding and fluid exudation from tissue, bond and repair tissue or organs injured during trauma or surgery, and avoid or minimize surgical sutures.

Chitosan is a natural, non-toxic, biodegradable polymer. Chitosan is composed of D-glucosamine linked to N-acetyl glucosamine groups via a $\beta \rightarrow (1,4)$ bond.

Biological properties of chitosan: chitosan has water-absorbing, moisturizing, antibacterial properties and is especially highly biocompatible, non-toxic and safe for the human body. In addition, chitosan is considered a substrate that facilitates cell growth to optimize the process of stimulation and tissue regeneration without causing harmful side effects to the body.

Biocompatibility of chitosan: A number of studies have been conducted to evaluate the compatibility of chitosan on many cell types such as fibroblasts, osteoblasts, chondrocytes, tissue cells, nerve cells, and liver cells. The results showed that chitosan is not cytotoxic and supports proliferation and development [1-4].

Antibacterial properties of chitosan: many studies have shown that chitosan fights bacteria Gram-positive and Gram-negative bacteria, fungi and yeast [5-7].

Applications of chitosan in biomedicine: Chitosan is used in the treatment of burns, chitosan is a substance added to dressings and has been approved for use on humans, chitosan with low molecular weight can be used as a carrier because of its ability to be easily bioabsorbed [8-9].

The present invention provides methods and technological approaches of producing the antibacterial modified chitosan-based hemostatic material, which produce the modified chitosan in form of powder, sponge, nanofiber, colloid, film, and other forms that satisfy various surgical hemostatic requirements, including ease of use.

The technical formulas of the present invention fulfill the foregoing performance requirements with modified chitosan applications as a biocompatible hemostatic material with characteristics that include dissolving or swelling in water and the subsequent formation of an adhesive glue or adhesive gel.

Natural raw chitosan has minimal hemostatic characteristics because the hydrophilic properties are unsatisfactory at room temperature.

The modified chitosan acquires certain chemical and physical characteristics by cutting, rearranging, or adding other chemical groups that change the structure of the raw chitosan molecular chain. The modified chitosan can be categorized primarily into physically modified chitosan, chemically modified chitosan, and enzymatically modified chitosan, according to the performed modification process.

The characteristics of the modified chitosan of the present invention further include the acquisition of hydrophilic groups in its molecular chains through the described modification process. When the hydrophilic and enhanced adhesive modified chitosan is applied to bleeding wound sites, it rapidly absorbs water in the blood and concentrates blood components. Concurrently, this interaction creates an adhesive matrix formed with the blood and plasma which adheres to the bleeding wound, mechanically seals broken blood vessels and stops bleeding.

The modified chitosan ingredient according to the present invention includes chitosan modified physically, chemically, or enzymatically, and chitosan modified repeatedly with at least one of the above methods or a combination of two or more of the above methods.

The antibacterial modified chitosan-based hemostatic material, according to the present invention, can be made in powder form or nanofibers form to be delivered directly to the bleeding wound surface.

In addition, the antibacterial modified chitosan-based hemostatic material of the present invention can be made into hemostatic sponge, nanofibers, film, and plaster, which can be applied to a bleeding wound site to stanch blood directly, wherein the hemostatic sponge, foam, the hemostatic film, and the hemostatic plaster can be made into a film or an attaching layer to the inside or surface of a fiber fabric, such as a bandage, band-aid; etc. Such hemostatic sponge, gauze hemostatic, hemostatic film, and hemostatic plaster can be columnar, sheet, massive, flocculent, or membranous.

Wherein, according to the present invention, other biocompatible hemostatic materials other than the modified chitosan can comprise one or more of the groups of gelatin, collagen, carboxymethyl cellulose, oxidized cellulose, oxidized regenerated cellulose, and starches. Whereas other known bioabsorbable hemostatic materials can be of one or more components, the modified chitosan can also be of one or more components, such as modified chitosan combined gelatin, modified chitosan combined collagen, modified chitosan combined thrombin, modified chitosan combined starch, modified chitosan combined carboxymethyl cellulose, and modified chitosan combined hyaluronic acid. These combinations can be molded into sponge, gauze, film, and plaster forms to satisfy clinical requirements.

According to another embodiment of the present invention, the antibacterial modified chitosan-based hemostatic material can further include other plasma substitutes by means of well-known pharmacokinetics approaches and specified physical/chemical properties to produce safe and reliable hemostatic agents.

When cationic chitosan of the modified chitosan ingredient is selected as a hemostatic material, the surface positive charge of the cationic chitosan attracts and interacts with electronegative blood erythrocytes, accelerating the blood coagulation process. Furthermore, when contacting blood, the positively charged modified chitosan adheres tightly to tissue, seals the wound, and rapidly stops bleeding. The cationic chitosan can be used independently as a hemostatic material or mixed with other modified chitosan ingredient as a composite hemostatic material. The mechanism for promoting tissue healing is the "glue" formation after the modified chitosan combined the biological peptides (PSK and PSP) contacts blood and establishes the "scaffold" on the wound surface which facilitates the adherence, growth, connection and propagation of tissue cells. In addition, local blood platelets are increasingly concentrated on the wound and, when activated, release tissue factors which promote healing.

It should also be noted that the term "dissolve/dissolving/dissolved" is used in the invention understood to mean the uniform distribution, or complete dissolution of, substances present in a solution/mixture.

It should also be noted that the term "biodegradable" is meant susceptible to breakdown by biological activity. For example, biodegradable chitosan compositions are susceptible to breakdown by enzymes present in vivo (e.g., lysozyme, N-acetyl-o-glucosaminidase and lipases). Degradation of a chitosan composition of the invention need not be complete. A chitosan composition of the invention may be degraded, for example, by the cleavage of one or more chemical bonds (e.g., glycosidic bonds).

In the embodiment of the present invention, percent mass or percentage (%) by weight=(mass of solute/mass of solution)×100%. The unit of mass is usually grams, or kilograms. Mass percent is also known as the correct percentage by weight or w/w %. It should also be noted that the molar mass is also within the meaning of the invention. Molar mass is the total mass of all atoms in a mole of compound. Total all volume percentages add up to 100%.

One embodiment of the invention is now described with reference to FIG. 1. FIG. 1 illustrates a conceptual block diagram of manufacturing the antibacterial modified chitosan-based hemostatic material 100 ("method 100") in accordance with an exemplary embodiment of the present invention. Method 100 includes a first stage 100A to create the homogeneous solution, a second stage 100B to create the antibacterial, antiviral solution, and a third stage 1000 to create the foundation mixture.

In the first stage of 100A, creating the homogeneous solution of at least three ingredients from ingredient A is a modified chitosan ingredient, ingredient B is a solution containing polysaccharide, and ingredient C is a solution containing dissolving solvent is intended to increase rapid hemostasis, and antibacterial activities. However, in an exemplary embodiment of the present invention, ingredient A, ingredient B, and the ingredient D are added in a specific order with a defined percentage (%) by weight. Namely, ingredient A admixed first, then ingredient B, and finally ingredient C. It should be noted that when ingredient A, ingredient B, and ingredient C are not admixed in the specific order described, the final product will not have rapid hemostasis, and antibacterial activities.

According to the embodiment of the present invention, prepare ingredient A comprising performing in a specific order from (A) to (C):
 (A) creating a chitin mixture by homogenously mixing 10 parts of a chitin ingredient from molting shell of shrimp with 1 part of a chitin ingredient from oyster mushroom; wherein the chitin mixture has a pH of 6.8-7.2;
 (B) centrifuging the chitin mixture at a speed of 3500-6500 rpm to separate the residue to obtain a temporary solution; and
 (C) adding (0.001-0.2) parts of Lactic anhydride into the temporary solution by dropped, adding (0.001-0.8) parts of pyridine solution combined with stirring at 50 rpm for 35 minutes, and adding (0.01-2.5) parts of ethanol solution 75% combined with stirring at 50 rpm for 5 minutes, then stop stirring and let stand for 30 minutes to obtain the modified chitosan ingredient.

According to the embodiment of the present invention, the chitin mixture is prepared according to patent application Ser. No. 18/818,636, entitled "A chitosan composition and method of manufacturing the same", filed on Aug. 29, 2024. Prepare the chitin ingredient from molting shell of shrimp comprising performing in a specific order from (a1) to (a3):
 (a1) collecting the molting shell of shrimp, then washing to remove impurities, and soaking with HCl solution in a ratio of 1:(3-5) (w/v) for 15-20 days, then filtering to remove liquid, washing twice with the 50% alcohol to obtain a first temporary mixture;
  in which molting shell of shrimp is selected from the group consisting of *litopenaeus vannamei* (*Penaeus vannamei*), *Penaeus monodon, Penaeus Merguiensis, Macrobrachium rosenbergi, Metapenaeus ensis, Macrobrachium lanchesteri, Fenneropenaeus Merguiensis, Penaeus Semisulcatus*, and a combination thereof;
 (a2) treating the first temporary mixture to obtain a basic solution including: dissolving a quicklime (CaO) ingredient in solution concentrated HCl contains 40% (concentrated grade) with combined stirring at 50 rpm for 5 minutes to obtain a solution 1;
  admixing the first temporary mixture to the solution 1 with combined stirring at 50 rpm for 5 minutes, then stop stirring and let stand for 7-10 days at 28° C.-40° C. to obtain the basic solution;
   wherein a ratio of the first temporary mixture and the quicklime (CaO) ingredient is 1:(2-5) (w/w);
   wherein a ratio of the quicklime (CaO) ingredient and the solution concentrated HCl contains 40% (concentrated grade) is 1:(2-5) (w/v);
 (a3) admixing 1 part of an enzyme solution into 10 parts of the basic solution, then stop stirring and let stand for 12-18 hours to obtain the chitin ingredient from molting shell of shrimp; wherein the enzyme solution comprises 3 parts of a protease ingredient with 1 part of a lipase ingredient, and (5000-10000) parts of the water.

Prepare the chitin ingredient from oyster mushroom comprising performing in a specific order from (b1) to (b4):
(b1) collecting oyster mushrooms, then washing to remove impurities, and soaking with a fruit vinegar in a ratio of 1:(3-5) (w/v) for 15-20 days, then filtering to remove liquid, and washing twice with the 50% alcohol to obtain a second temporary mixture; wherein the fruit vinegar has a concentration of 35%-55%;
in which oyster mushrooms are selected from the group consisting of *pleurotus pulmonarius, Pleurotus* cf. *floridanus, Pleurotus ostreatus, Pleurotus citrinopileutus*, and a combination thereof;
(b2) treating the second temporary mixture to obtain a basic temporary solution including:
dissolving the quicklime (CaO) ingredient in solution concentrated HCl contains 40% (concentrated grade) with combined stirring at 50 rpm for 5 minutes to obtain the solution 1;
admixing the second temporary mixture to the solution 1 with combined stirring at 50 rpm for 5 minutes, then stop stirring and let stand for 7-10 days at 28° C.-40° C. to obtain the basic temporary solution;
wherein a ratio of the second temporary mixture and the quicklime (CaO) ingredient is 1:(3-5) (w/w);
wherein the ratio of the quicklime (CaO) ingredient and the solution concentrated HCl contains 40% (concentrated grade) is 1:(2-5) (w/v);
(b3) admixing the microorganism solution at step (i) into the basic temporary solution at a ratio of (1-2): 10 (w/v) to obtain a foundation temporary solution; and
(b4) adjusting pH of the foundation temporary solution reached 6.8-7.2, then fermenting at 30° C.-40° C. for 125-135 hours to obtain the chitin temporary mixture from oyster mushroom.

According to the embodiment of the present invention, at step (C), adding (0.01-0.1) parts of Lactic anhydride into the temporary solution by dropped.

According to the embodiment of the present invention, at step (C), adding (0.01-0.1) parts of Lactic anhydride into the temporary solution by dropped.

According to the embodiment of the present invention, prepare ingredient B by mixing a Polysaccharopeptide (PSP) component is extracted from a solution of turkey tail mushroom extract with a first percentage (%) by weight and a Polysaccharide K (PSK) component is extracted from the solution of turkey tail mushroom extract with a second percentage (%) by weight, combining stirring for 10 minutes.

According to the embodiment of the present invention, the solution of turkey tail mushroom extract, and is prepared according to patent No. U.S. Ser. No. 12/042,521 B1, entitled "A method for producing a complex composition of turkey tail mushroom extract—chitosan", filed on Mar. 1, 2024. Prepare the solution of turkey tail mushroom extract comprising performing in a specific order from (A') to (D'):
(A') fermenting a turkey tail mushroom mixture with the addition of a microorganism preparations in ratio (45-55): 1 at 30° C.-35° C. combined with stirring at 120 rpm for 35-40 hours, and centrifuging at a speed of 6000 rpm for 60 minutes to obtain a first solution and a first residue;
wherein the turkey tail mushroom mixture comprising
(1-2) parts a first turkey tail mushroom component with
(1-2) parts a second turkey tail mushroom component,
(1-2) parts a third turkey tail mushroom component,
(1-2) parts a fourth turkey tail mushroom component, and (1-2) parts a fifth turkey tail mushroom component;
the first turkey tail mushroom component is obtained by cultivating *Trametes versicolor* (L.) Pilat on biomass growth medium;
the second turkey tail mushroom component is obtained by cultivating *Trametes versicolor* (L.) Lioud (1920) on biomass growth medium;
the third turkey tail mushroom component is obtained by cultivating *Trametes sanguinea* (L.) Imazeki on biomass growth medium;
the fourth turkey tail mushroom component is obtained by cultivating *Trametes versicolor* BRG04 on biomass growth medium;
the fifth turkey tail mushroom component is obtained by cultivating Pycnoporus *sanguineus* (L.: Fr.) Murrill on biomass growth medium; and
the biomass growth medium comprising: glucose having 30 g/L, peptone having 4 g/L, magnesium sulfate ($MgSO_4$) having 0.5 g/L, and potassium dihydrogen phosphate ($KH_2PO_4$) having 1 g/L.
wherein the microorganism preparations comprising (1-3) parts a first nutrient broth solution with (1-3) parts a second nutrient broth solution, and (1-3) parts a third nutrient broth solution;
the first nutrient broth solution cultivating *Lactobacillus plantarum* (identified on the gene bank as JQ937330.1) on LB medium;
the second nutrient broth solution cultivating *Lactobacillus acidophilus* (identified on the gene bank as OK398226.1) on LB medium; and
the third nutrient broth solution cultivating *Bacillus subtilis* (identified on the gene bank as KY777343.1) on LB medium;
(B') extracting the first residue with water at a ratio of 1:(5-7) at 100° C. for 10-15 minutes to obtain a second solution and a second residue;
(C') extracting the first residue with water at a ratio of 1:(5-7) at 55° C. for 2 hours, then filtering to remove residue, and neutralizing pH to 6.8-7.2 to obtain a third solution; and
(D') mixing the first solution with the second solution, and the third solution to obtain the solution of turkey tail mushroom extract.

According to the embodiment of the present invention, the polysaccharopeptide (PSP) component is extracted from the solution of turkey tail mushroom extract comprising performing in a specific order from (a) to (b):
(a) mixing the solution of turkey tail mushroom extract with water at a ratio of 1/32 with stirring at 1000 rpm for 5 minutes, then extracting at 121° C. for 35 minutes, then adding ammonium salt saturated sulfate 80% into said extract at ratio of 1:3 and overnight at 4° C. to form precipitate, and centrifuging at a speed of 8000 rpm for 15 minutes to collect a first precipitate; and
(b) dissolving the first precipitate with water at a ratio of 1:5, then filtering by the membrane filter having a pore size of 30 Kda to collect a fraction that does not pass through the membrane filter, and drying the fraction at 35° C.-42° C. for 35 hours to obtain the polysaccharopeptide (PSP) component.

According to the embodiment of the present invention, the Polysaccharide K (PSK) component is extracted from the solution of turkey tail mushroom extract comprising performing in a specific order from (a') to (b'):
(a') mixing the turkey tail mushroom extract ingredient with water at a ratio of 1/32 with stirring at 1000 rpm for 5 minutes, then extracting at 121° C. for 45 minutes, then adding ethanol solution 60% into said extract at ratio of 1:3 and overnight at 4° C. to form precipitate, and centrifuging at a speed of 8000 rpm for 25 minutes to collect a second precipitate; and (b') washing the second precipitate by ethanol solution 60%, then drying at 35° C.-42° C. for 28 hours to obtain the the Polysaccharide K (PSK) component.

According to the embodiment of the present invention, prepare the solution containing dissolving solvent by dissolving water and Tween 80 with a third percentage (%) by weight at 45° C. combining stirring for 15 minutes, then continue to add Dimethyl Sulfoxide (DMSO) solution with a fourth percentage (%) by weight, PEG-400 (Poly Ethylene Glycol-400) with a fifth percentage (%) by weight and hyaluronic acid solution with a sixth percentage (%) by weight, combining with stirring for 20 minutes at 45° C.

Within the scope of the present invention, the term "homogeneous solution" includes the following meanings:
(a") the homogeneous solution is a solution that completely dissolves ingredient A, ingredient B, and ingredient C to create a new preparation have rapid hemostasis, and antibacterial activities;
(b") the homogeneous solution is a solution that completely dissolve the modified chitosan ingredient, the polysaccharopeptide (PSP) component, the polysaccharide K (PSK) component, Dimethyl Sulfoxide (DMSO) solution, Tween 80, PEG-400 (Poly Ethylene Glycol-400), the hyaluronic acid solution, and water having the correct percentage (%) by weight;
(c") the homogeneous solution mixes act as a reactant, allowing the addition of ingredients to contribute their chemical and physical properties to create a new preparation; and
(d") the homogeneous solution chemically bonds with the ingredient D, and the composition of other supplements including but not limited to ionization reactions, covalent reactions, reducing reactions, replacement reactions, and rearrangement reactions to form a new chemical composition.

Still with FIG. 1, continue to the second stage of 100B, when the homogeneous solution is mixed with ingredient D at 1500 rpm for 5-20 minutes at 28° C.-38° C., to obtain a foundation mixture; in which ingredient D is a solution containing nano silver. In particular, the solution containing nano silver is added or reacted or dissolve uniformly with the homogeneous solution by a magnetic stirrer or other similar device. Magnetic stirrer has been known in previous art so the description of the structure and its operating principle will not be described in detail in the invention. It should be noted that the term "admixed/mixed/admixing/mixing" as used in the present invention is understood to mean adding, or reacting, or dissolving homogeneously, or evenly, components in the same solution/mixture.

According to the embodiment of the present invention, prepare the solution containing nano silver by performing a blend of a solution extracted from plants with a seventh percentage (%) by weight, an aqueous soluble silver salt with a eighth percentage (%) by weight, then treating by ultrasonic with amplitude 25% at 35° C.-42° C. for 10 minutes, and adding an alginate solution 1% with a ninth percentage (%) by weight, and an ascorbic acid solution with a tenth percentage (%) by weight, combined with stirring at 55° C.-60° C. for 20 minutes.

As the plant extract in the present invention, an "extracts/essential" extracted as an aromatic substance contained in the above-mentioned plants is preferable. The essential oil in a narrow sense obtained by steam distillation from the above plants or dried materials thereof is preferably used as the "extracts/essential oil" in the present invention, but is not limited thereto. For example, oils extracted from the plants by using other methods such as extraction or expression are also included in the "extracts/essential oil" of the present invention as long as they contain essential oil components (such as aromatic substances). As other methods for extracting essential oils from plants, for example, solvent extraction (such as alcohol extraction, organic solvent extraction), oil and fat adsorption extraction (hot enfleurage or cold enfleurage), and supercritical fluid extraction are known. When the steam distillation cannot be applied because of a low essential oil content in the plant and the like, the solvent extraction is often used. Examples of the solvent used for extraction include, but are not limited to, alcohols such as ethanol, methanol, propanol, isopropanol, and butanol, and organic solvents including relatively high polarity solvents such as acetone and low polarity solvents such as hexane. The "extracts/essential oil" in the present invention may be those in which the oil obtained by the above method is further purified and concentrated by using various purification procedures such as hydrophobic or adsorptive chromatography using a support such as porous beads, silica gel, or alumina.

According to the embodiment of the present invention, the solution extracted from plants is prepared by sequentially mixing in a container a lotus leaf extract/essential oil, of a grapefruit peels extract/essential oil, a piper seeds extract/essential oil, an *ardisia* leaf extract/essential oil, a *Gomphrena celosioides* Mart. extract/essential oil to form a mixture, and a *Selaginella tamariscina* (Beauv.) Spring extract/essential oil; wherein after each addition of an extract/essential oil the mixture is stirred until the mixture is homogenous.

According to the embodiment of the present invention, the piper seeds extract/essential oil is extracted from piper seeds crushed or not crushed, and immersed in solvent, or saturated brine solution; in which piper seeds including *Piper nigrum* L., *Piper bavinum* C. DC., *Piper saxicola* C. DC., *Piper gymnostachyum* C. DC., *Piper brevicaule* C. DC., *Piper pierrei* C. DC, *Piper boehmeriifolium* (Miq.) Wall. ex C. DC., and *Piper retrofractum* Vahl.

According to the embodiment of the present invention, the *ardisia* leaf extract/essential oil is extracted from *ardisia* leaf crushed/chopped/or not chopped, and immersed in solvent, or saturated brine solution; in which *ardisia* leaf including *Ardisia balansana* Yang, *Ardisia caudata* Hemsl., *Ardisia incarnata* Pitard, *Ardisia insularis* Mez., *Ardisia maculosa* Mer., *Ardisia primulifolia* Gardn., *Ardisia pseudocrispa* Pit., *Ardisia splendens* Pit., and *Ardisia tsangii* E. Walker.

According to the embodiment of the present invention, the aqueous soluble silver salt is selected from the group consisting of silver acetate, silver fluogallate, silver nitrate, and silver sulfate; in which aqueous soluble silver salt has a concentration of 0.02 M.

According to the preferred embodiment of the present invention, the aqueous soluble silver salt is silver nitrate 0.02M.

In many aspects of the present invention, the foundation mixture obtained at the second stage 100B is defined as a mixture with the following functions:
(a''') the foundation mixture is a solution that completely dissolves ingredient A, ingredient B, ingredient C, and ingredient D to create a new preparation have rapid hemostasis, and antibacterial activities;
(b''') the foundation mixture is a solution that completely dissolve the polysaccharopeptide (PSP) component, the polysaccharide K (PSK) component, Dimethyl Sulfoxide (DMSO) solution, Tween 80, PEG-400 (Poly Ethylene Glycol-400), the hyaluronic acid solution, the solution extracted from plants, the aqueous soluble silver salt, the alginate ingredient, the ascorbic acid solution, the modified chitosan ingredient, and water having the correct percentage (%) by weight; and (c''') the foundation mixture mixes act as a reactant, allowing the addition of ingredients to contribute their chemical and physical properties to create a new preparation.

According to the embodiment of the present invention, the antibacterial modified chitosan-based hemostatic material is made by method 100 depending on the percentages (%) of each of the ingredients listed in detail in Table 1 below, including a first formula, a second formula, a third formula, and a fourth formula; and in which the third formula is stronger than the first formula, the second formula is stronger than the fourth formula and the first formula is stronger than the second formula; in which the comparative factor is rapid hemostasis, and antibacterial activities.

TABLE 1

Mixed ingredients to creating the antibacterial modified chitosan-based hemostatic material according to the embodiment of the invention

| No. | Name of | First formula | Second formula | Third formula | Fourth formula |
|---|---|---|---|---|---|
| | | Percentage (%) by weight | | | |
| 1 | The modified chitosan ingredient | 50-85 | 50-85 | 50-85 | 50-85 |
| 2 | The polysaccharopeptide (PSP) component | 0.1-0.4 | 0.6-0.9 | 0.1-0.5 | 0.6-0.9 |
| 3 | The polysaccharide K (PSK) component | 0.6-0.9 | 0.1-0.4 | 0.1-0.5 | 0.6-0.9 |
| 4 | Dimethyl Sulfoxide (DMSO) solution | 0.13-1.5 | 0.13-1.5 | 0.13-1.5 | 0.13-1.5 |
| 5 | Tween 80 | 0.008-0.08 | 0.008-0.08 | 0.008-0.08 | 0.008-0.08 |
| 6 | PEG-400 | 0.03-0.18 | 0.03-0.18 | 0.03-0.18 | 0.03-0.18 |
| 7 | The hyaluronic acid solution | 0.005-0.05 | 0.005-0.05 | 0.005-0.05 | 0.005-0.05 |
| 8 | The solution extracted from plants | 0.1-0.25 | 0.1-0.25 | 0.1-0.25 | 0.1-0.25 |
| 9 | The aqueous soluble silver salt | 0.08-0.27 | 0.08-0.27 | 0.08-0.27 | 0.08-0.27 |
| 10 | The alginate ingredient | 0.3-0.65 | 0.3-0.65 | 0.3-0.65 | 0.3-0.65 |
| 11 | The ascorbic acid solution | 0.001-0.005 | 0.001-0.005 | 0.001-0.005 | 0.001-0.005 |
| 12 | Water | rest | rest | rest | rest |

Figure 2:
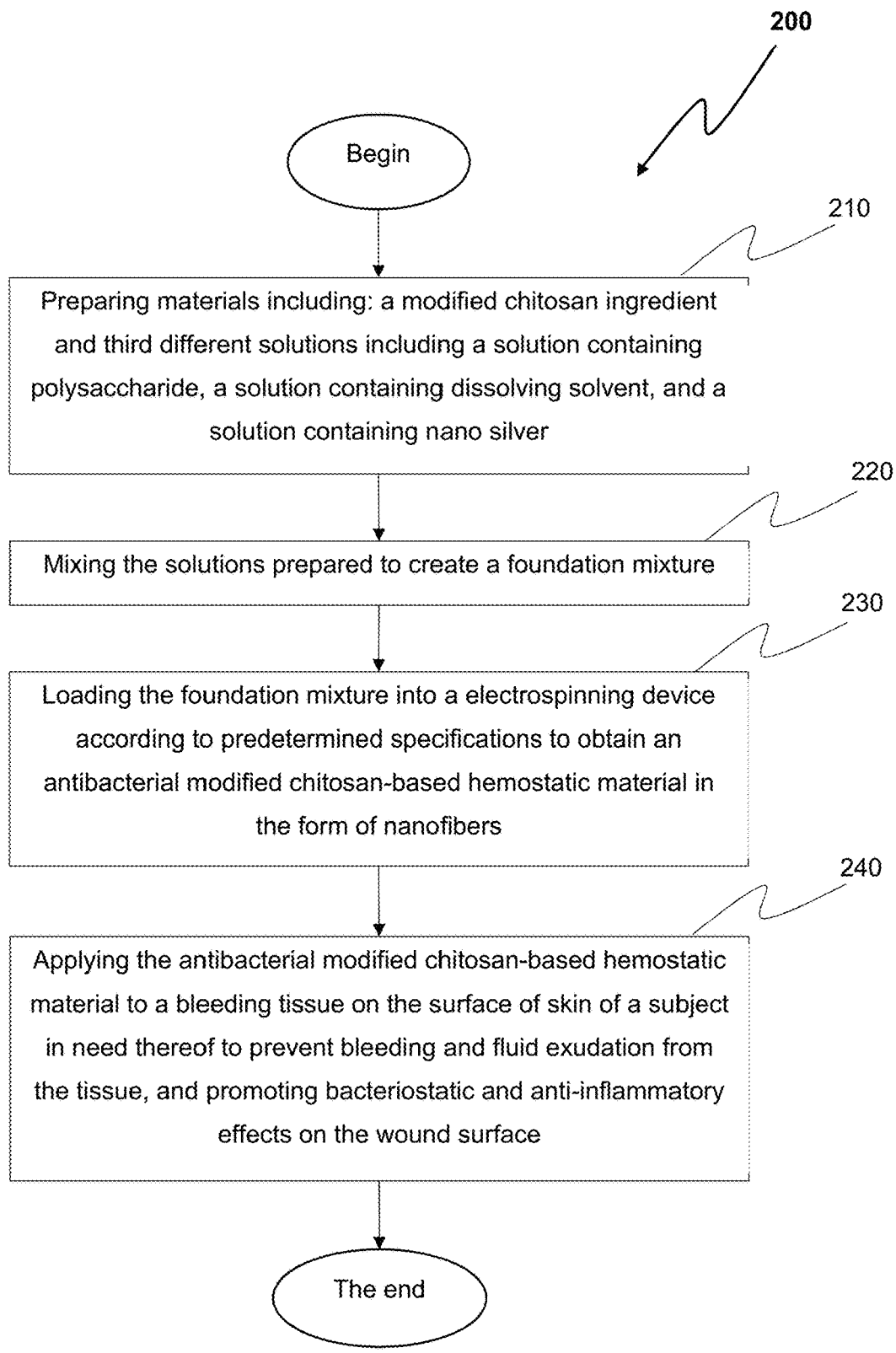
FIG. 2 is a flowchart illustrating a method of manufacturing the antibacterial modified chitosan-based hemostatic material according to an embodiment of the present invention.

Now referring to FIG. 2, the method of manufacturing the antibacterial modified chitosan-based hemostatic material 200 ("method 200") based on the above principle in accordance with an exemplary embodiment of the present invention. In particular, method 200 includes the following steps:

At step 210, preparing materials including: a modified chitosan ingredient and third different solutions including a solution containing polysaccharide, a solution containing dissolving solvent, and a solution containing nano silver.

According to the embodiment of the present invention, prepare the modified chitosan ingredient similar to preparing ingredient A as described in detail in the first stage 100A according to method 100 above.

According to the embodiment of the present invention, prepare the solution containing polysaccharide similar to preparing ingredient B as described in detail in the first stage 100A according to method 100 above.

According to the embodiment of the present invention, prepare the solution containing dissolving solvent similar to preparing ingredient C as described in detail in the first stage 100A according to method 100 above.

According to the embodiment of the present invention, prepare the solution containing dissolving solvent similar to preparing ingredient D as described in detail in the second stage 100A according to method 100 above.

At step 220, mixing the solutions prepared in step 210 in two stages:
 a stage 1: creating a homogeneous solution by mixing the prepared solutions in the order that the modified chitosan ingredient, the solution containing polysaccharide, and the solution containing dissolving solvent; wherein after each addition of said ingredient mixed at 28° C.-38° C. with stirring at 500-1000 rpm for 5-20 minutes; and
 a stage 2: admixing the solution containing nano silver into the homogeneous solution with combined stirring at 1500 rpm for 5-20 minutes at 28° C.-38° C., to obtain a foundation mixture.

At step 230, loading the foundation mixture into a electrospinning device according to predetermined specifications to obtain the antibacterial modified chitosan-based hemostatic material in the form of nanofibers; wherein predetermined specifications including: injection speed 0.8-1.4 mL/h, voltage 12-20 kV, collection distance 8-21 cm, and rolling speed at 30-50 rpm.

According to the embodiment of the present invention, at step 230 predetermined specifications including: injection speed 1-1.2 mL/h, voltage 15-18 kV, collection distance 10-14 cm, and rolling speed at 40-45 rpm.

According to the preferred embodiment of the present invention, at step 230 predetermined specifications including: injection speed 1.2 mL/h, voltage 16 kV, collection distance 12 cm, and rolling speed at 45 rpm.

In some embodiments, the foundation mixture is loaded into a 10 mL syringe with a blunt 18G, stainless steel needle tip. The syringe is loaded into the electrospinning apparatus and the flow rate set to a speed appropriate to the desired diameter size, e.g. 0.8-1.4 mL/h. The solution is electrospun at about 12-20 kV and the fibers are collected on a target (such as about 38.2-50 cm diameter circular disc of non-stick aluminum foil). The target is positioned about 10-14 cm from the needle tip and rotated at about 40-45 rpm by a motor to ensure even and random distribution of fibers. The electrospinning apparatus is housed inside a ventilated box, which is vented, preferably to the fume hood. After electrospinning, the nanofibrous membrane is vacuum treated for several hours, e.g. overnight, to remove residual solvent. It should also be noted that the term "electrospin" or "electrospinning" is meant include, but are not limited to a process of producing chitosan nanofibers from a solution of chitosan by applying an electric charge to the chitosan solution.

According to another embodiment of the invention, at step 230 further comprising, before the loading, dissolving the foundation mixture with a solvent; wherein the solvent includes dimethylacetamide (DMAc), acetone (Ac), acid trifluoroacetic (TFA), acid acetic, acid citric, acid oxalic, acid proprionic, acid ascorbic, acid hydrochloric, acid formic, acid salicylic, acid lactic, dichloromethane (DCM), ethyl acetate (EA), tetrahydrofuran (THF), dimethylformamide (DMF), ethylene chloride, tannin, and a combination thereof.

According to the embodiment of the present invention, the solvent combination including: acid hydrochloric and dimethylacetamide (DMAc), acid hydrochloric and acetone (Ac), acid hydrochloric and acid trifluoroacetic (TFA), acid hydrochloric and acid acetic, acid hydrochloric and acid citric, acid hydrochloric and acid oxalic, acid hydrochloric and acid proprionic, acid hydrochloric and acid ascorbic, acid hydrochloric and acid formic, acid hydrochloric and acid salicylic, acid hydrochloric and acid lactic, acid hydrochloric and dichloromethane (DCM), acid hydrochloric and ethyl acetate (EA), acid hydrochloric and tetrahydrofuran (THF), acid hydrochloric and dimethylformamide (DMF), acid hydrochloric and ethylene chloride, and acid hydrochloric and tannin.

According to the embodiment of the present invention, the antibacterial modified chitosan-based hemostatic material is made by method 200 depending on the percentages (%) of each of the ingredients listed in detail in Table 1 including a first formula, a second formula, a third formula, and a fourth formula; in which the third formula is stronger than the first formula, the second formula is stronger than the fourth formula and the first formula is stronger than the second formula; in which the comparative factor is rapid hemostasis, and antibacterial activities.

According to the embodiment of the present invention, the percentage (%) of each ingredient that makes the first formula of antibacterial modified chitosan-based hemostatic material comprises:
the polysaccharopeptide (PSP) component having 0.1%-0.4% by weight;
the polysaccharide K (PSK) component having 0.6%-0.9% by weight;
Dimethyl Sulfoxide (DMSO) solution having 0.13%-1.5% by weight;
Tween 80 having 0.008%-0.08% by weight;
PEG-400 (Poly Ethylene Glycol-400) having 0.03%-0.18% by weight;
the hyaluronic acid solution having 0.005%-0.05% by weight;
the solution extracted from plants having 0.1%-0.25% by weight; wherein the solution extracted from plants including: 0.015%-0.075% by weight of the lotus leaf extract/essential oil, 0.012%-0.06% by weight of the grapefruit peels extract/essential oil, 0.005%-0.76% by weight of the piper seeds extract/essential oil, 0.082%-0.045% by weight of the *ardisia* leaf extract/essential oil, 0.001%-0.05% by weight of the *Gomphrena celosioides* Mart. extract/essential oil, and 0.003%-0.084% by weight of the *Selaginella tamariscina* (Beauv.) Spring extract/essential oil;
the aqueous soluble silver salt having 0.08%-0.27% by weight;
the alginate ingredient 1% having 0.3%-0.65% by weight;
the ascorbic acid solution having 0.001%-0.005% by weight;
the modified chitosan ingredient having 50%-85% by weight; and
the remainder is the water.

According to the embodiment of the present invention, the percentage (%) of each ingredient that makes the second formula of antibacterial modified chitosan-based hemostatic material comprises:
the polysaccharopeptide (PSP) component having 0.6%-0.9% by weight;
the polysaccharide K (PSK) component having 0.1%-0.4% by weight;
Dimethyl Sulfoxide (DMSO) solution having 0.13%-1.5% by weight;
Tween 80 having 0.008%-0.08% by weight;
PEG-400 (Poly Ethylene Glycol-400) having 0.03%-0.18% by weight;
the hyaluronic acid solution having 0.005%-0.05% by weight;
the solution extracted from plants having 0.1%-0.25% by weight; wherein the solution extracted from plants including: 0.015%-0.075% by weight of the lotus leaf extract/essential oil, 0.012%-0.06% by weight of the grapefruit peels extract/essential oil, 0.005%-0.76% by weight of the piper seeds extract/essential oil, 0.082%-0.045% by weight of the *ardisia* leaf extract/essential oil, 0.001%-0.05% by weight of the *Gomphrena celosioides* Mart. extract/essential oil, and 0.003%-0.084% by weight of the *Selaginella tamariscina* (Beauv.) Spring extract/essential oil;
the aqueous soluble silver salt having 0.08%-0.27% by weight;
the alginate ingredient 1% having 0.3%-0.65% by weight;
the ascorbic acid solution having 0.001%-0.005% by weight;
the modified chitosan ingredient having 50%-85% by weight; and the remainder is the water.

According to the embodiment of the present invention, the percentage (%) of each ingredient that makes the third formula of antibacterial modified chitosan-based hemostatic material comprises:
the polysaccharopeptide (PSP) component having 0.1%-0.5% by weight;
the polysaccharide K (PSK) component having 0.1%-0.5% by weight;
Dimethyl Sulfoxide (DMSO) solution having 0.13%-1.5% by weight;
Tween 80 having 0.008%-0.08% by weight;
PEG-400 (Poly Ethylene Glycol-400) having 0.03%-0.18% by weight;
the hyaluronic acid solution having 0.005%-0.05% by weight;
the solution extracted from plants having 0.1%-0.25% by weight; wherein the solution extracted from plants including: 0.015%-0.075% by weight of the lotus leaf extract/essential oil, 0.012%-0.06% by weight of the grapefruit peels extract/essential oil, 0.005%-0.76% by weight of the piper seeds extract/essential oil, 0.082%-0.045% by weight of the *ardisia* leaf extract/essential oil, 0.001%-0.05% by weight of the *Gomphrena celosioides* Mart. extract/essential oil, and 0.003%-0.084% by weight of the *Selaginella tamariscina* (Beauv.) Spring extract/essential oil;

the aqueous soluble silver salt having 0.08%-0.27% by weight;

the alginate ingredient 1% having 0.3%-0.65% by weight;

the ascorbic acid solution having 0.001%-0.005% by weight;

the modified chitosan ingredient having 50%-85% by weight; and the remainder is the water.

According to the embodiment of the present invention, the percentage (%) of each ingredient that makes the fourth formula of antibacterial modified chitosan-based hemostatic material comprises:

the polysaccharopeptide (PSP) component having 0.6%-0.9% by weight;

the polysaccharide K (PSK) component having 0.6%-0.9% by weight;

Dimethyl Sulfoxide (DMSO) solution having 0.13%-1.5% by weight;

Tween 80 having 0.008%-0.08% by weight;

PEG-400 (Poly Ethylene Glycol-400) having 0.03%-0.18% by weight;

the hyaluronic acid solution having 0.005%-0.05% by weight;

the solution extracted from plants having 0.1%-0.25% by weight; wherein the solution extracted from plants including: 0.015%-0.075% by weight of the lotus leaf extract/essential oil, 0.012%-0.06% by weight of the grapefruit peels extract/essential oil, 0.005%-0.76% by weight of the piper seeds extract/essential oil, 0.082%-0.045% by weight of the *ardisia* leaf extract/essential oil, 0.001%-0.05% by weight of the *Gomphrena celosioides* Mart. extract/essential oil, and 0.003%-0.084% by weight of the *Selaginella tamariscina* (Beauv.) Spring extract/essential oil;

the aqueous soluble silver salt having 0.08%-0.27% by weight;

the alginate ingredient 1% having 0.3%-0.65% by weight;

the ascorbic acid solution having 0.001%-0.005% by weight;

the modified chitosan ingredient having 50%-85% by weight; and the remainder is the water.

Still with FIG. 2, at step 240, applying the antibacterial modified chitosan-based hemostatic material at step 230 to a bleeding tissue on the surface of skin of a subject in need thereof to prevent bleeding and fluid exudation from the tissue, and promoting bacteriostatic and anti-inflammatory effects on the wound surface.

According to the embodiment of the present invention, the bleeding tissue of the subject is selected from the group consisting of mammals, birds, and reptiles.

According to the embodiment of the present invention, the bleeding tissue of mammals is human.

According to the embodiment of the present invention, the antibacterial modified chitosan-based hemostatic material containing hydrophilic group, pH is 7.5-8.5, adhesion 35-50 mPas at 36° C.-38° C., and has an in vitro clotting time of less than 50 s for its use to treat a bleeding tissue of animal that forms a modified chitosan-blood coagulation matrix upon contacting the bleeding tissue.

In addition, the results of analysis on bactericidal and safety of the antibacterial modified chitosan-based hemostatic material were created by method 200 was tested on toxicity. The toxicity (0.01 mL/20 g body weight, applied to the skin on the back for 30 days) in mice did not affect the erythrocyte parameters, AST, ALT, and creatinine. The composition increased the number of white blood cells, but did not affect the percentage of MID cells, monocytes, Granulocytes compared with the control batch using the solvent. At the same time, there were no differences in the microstructural characteristics of the liver and kidneys of the mice when using the composition compared to the control using the solvent.

The antibacterial modified chitosan-based hemostatic material of the present invention is tested for biological activity including antioxidant test by DPPH free radical scavenging and resistance to lipid peroxidation, and antimicrobial activity tests are listed in Table 2 below.

TABLE 2

Results of biological activity testing of the antibacterial modified chitosan-based hemostatic material according to the embodiment of the present invention

| No | Biological activity testing | Result |
|---|---|---|
| 1 | DPPH free radical scavenging | (+) |
| 2 | Resistance to lipid peroxidation | (+) |
| 3 | Antimicrobial activity | *Staphylococcus aureus, Escherichia coli, Candida albicans, Pseudomonas aeruginosa, Bacillus subtilis* | wherein, (+) is a positive sample, having DPPH free radical scavenging/lipid Resistance to lipid peroxidation greater than 50%.

In addition, the results of compared the external thrombotest between four formulas of the antibacterial modified chitosan-based hemostatic material and the common medical absorbent cotton, listed in Table 3 below.

TABLE 3

The results compared the external thrombotest between four formulas of the antibacterial modified chitosan-based hemostatic material and the common medical absorbent cotton

| Name of | Clotting time (second) |
|---|---|
| The common medical absorbent cotton | 372 ± 15 |
| The first formula | 48 ± 2 |
| The second formula | 55 ± 2 |
| The third formula | 36 ± 2 |
| The fourth formula | 60 ± 3 |

From Table 3 it can be seen that compared with the common medical absorbent cotton, by prepared by preparation method disclosed by the invention four formulas of the antibacterial modified chitosan-based hemostatic material substantially shortens the clotting time, and the four formulas of the antibacterial modified chitosan-based hemostatic material prepared by the present invention can improve antihemorrhagic performance. Especially, the third formula of the antibacterial modified chitosan-based hemostatic material has shorter clotting time than the remaining three formulas.

Surveying oxygen transmission rate of four formulas of the antibacterial modified chitosan-based hemostatic material. Using the Winkler method for analyzed of dissolved oxygen content in water. The steps are as follows: 200 mL of distilled water cooled after boiling was added to a 250 mL-stop flask, and then the antibacterial modified chitosan-based hemostatic material film was placed on the mouth of the flask and sealed, and the permeability of oxygen was measured. After being left in an open environment for 24 hours, calculating dissolved oxygen content in water, as a result as shown in Table 4 below.

TABLE 4

The results oxygen transmission rate of the four formulas of the antibacterial modified chitosan-based hemostatic material

| Name of | Oxygen transmission rate (mg/mL) |
|---|---|
| The first formula | 11 |
| The second formula | 10.55 |
| The third formula | 11.48 |
| The fourth formula | 12.7 |

From Table 4 it can be seen that the four formulas of the antibacterial modified chitosan-based hemostatic material prepared by the present invention can improve oxygen transmission rate, is suitable for cell regeneration, and helps to accelerate the healing process.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

REFERENCES

1. Lahiji, A., et al., Chitosan supports the expression of extracellular matrix proteins in human osteoblasts and chondrocytes. Journal of Biomedical Materials Research Part A, 2000. 51(4): p. 586-595.
2. Howling, G. I., et al., The effect of chitin and chitosan on the proliferation of human skin fibroblasts and keratinocytes in vitro. Biomaterials, 2001. 22(22): p. 2959-2966.
3. Jiang, T., et al., Chitosan as a biomaterial: structure, properties, and applications in tissue engineering and drug delivery, in Natural and synthetic biomedical polymers. 2014, Elsevier. p. 91-113.
4. Amera, A., et al., Synthesis and characterization of porous biphasic calcium phosphate scaffold from different porogens for possible bone tissue engineering applications. Science of Sintering, 2011. 43(2): p. 183-192.
5. Jiang, T., et al., Chitosan as a biomaterial: structure, properties, and applications in tissue engineering and drug delivery, in Natural and synthetic biomedical polymers. 2014, Elsevier. p. 91-113.
6. Chen, C.-S., W.-Y. Liau, and G.-J. Tsai, Antibacterial effects of N-sulfonated and N-sulfobenzoyl chitosan and application to oyster preservation. Journal of Food Protection, 1998. 61(9): p. 1124-1128.
7. Jung, B. O., et al., Preparation of amphiphilic chitosan and their antimicrobial activities. Journal of Applied Polymer Science, 1999. 72(13): p. 1713-1719.
8. Kumar, M. N. R., A review of chitin and chitosan applications. Reactive functional polymers, 2000. 46(1): p. 1-27.
9. Lahiji, A., et al., Chitosan supports the expression of extracellular matrix proteins in human osteoblasts and chondrocytes. Journal of Biomedical Materials Research Part A, 2000. 51(4): p. 586-595.

What is claimed is:

1. A method of manufacturing the antibacterial modified chitosan-based hemostatic material comprising steps performed in the following specific order:
   (i) preparing materials including: a modified chitosan ingredient and third different solutions including a solution containing polysaccharide, a solution containing dissolving solvent, and a solution containing nano silver;
   in which, prepare the modified chitosan ingredient comprising performing in a specific order from (A) to (C):
   (A) creating a chitin mixture by homogenously mixing 10 parts of a chitin ingredient from molting shell of shrimp with 1 part of a chitin ingredient from oyster mushroom; wherein the chitin mixture has a pH of 6.8-7.2;

in which, prepare the chitin ingredient from molting shell of shrimp comprising performing in a specific order from (a1) to (a3):

(a1) collecting the molting shell of shrimp, then washing to remove impurities, and soaking with HCl solution in a ratio of 1:(3-5) (w/v) for 15-20 days, then filtering to remove liquid, washing twice with the 50% alcohol to obtain a first temporary mixture;

in which molting shell of shrimp is selected from the group consisting of litopenaeus vannamei (Penaeus vannamei), Penaeus monodon, Penaeus Merguiensis, Macrobrachium rosenbergi, Metapenaeus ensis, Macrobrachium lanchesteri, Fenneropenaeus Merguiensis, Penaeus Semisulcatus, and a combination thereof;

(a2) treating the first temporary mixture to obtain a basic solution including:

dissolving a quicklime (CaO) ingredient in solution concentrated HCl contains 40% (concentrated grade) with combined stirring at 50 rpm for 5 minutes to obtain a solution 1;

admixing the first temporary mixture to the solution 1 with combined stirring at 50 rpm for 5 minutes, then stop stirring and let stand for 7-10 days at 28° C.-40° C. to obtain the basic solution;

wherein a ratio of the first temporary mixture and the quicklime (CaO) ingredient is 1:(2-5) (w/w);

wherein a ratio of the quicklime (CaO) ingredient and the solution concentrated HCl contains 40% (concentrated grade) is 1:(2-5) (w/v);

(a3) admixing 1 part of an enzyme solution into 10 parts of the basic solution, then stop stirring and let stand for 12-18 hours to obtain the chitin ingredient from molting shell of shrimp;

wherein the enzyme solution comprises 3 parts of a protease ingredient with 1 part of a lipase ingredient, and (5000-10000) parts of the water;

in which prepare the chitin ingredient from oyster mushroom comprising performing in a specific order from (b1) to (b4):

(b1) collecting oyster mushrooms, then washing to remove impurities, and soaking with a fruit vinegar in a ratio of 1:(3-5) (w/v) for 15-20 days, then filtering to remove liquid, and washing twice with the 50% alcohol to obtain a second temporary mixture; wherein the fruit vinegar has a concentration of 35%-55%;

in which oyster mushrooms are selected from the group consisting of pleurotus pulmonarius, Pleurotus cf. floridanus, Pleurotus ostreatus, Pleurotus citrinopileutus, and a combination thereof;

(b2) treating the second temporary mixture to obtain a basic temporary solution including:

dissolving the quicklime (CaO) ingredient in solution concentrated HCl contains 40% (concentrated grade) with combined stirring at 50 rpm for 5 minutes to obtain the solution 1;

admixing the second temporary mixture to the solution 1 with combined stirring at 50 rpm for 5 minutes, then stop stirring and let stand for 7-10 days at 28° C.-40° C. to obtain the basic temporary solution;

wherein a ratio of the second temporary mixture and the quicklime (CaO) ingredient is 1:(3-5) (w/w);

wherein the ratio of the quicklime (CaO) ingredient and the solution concentrated HCl contains 40% (concentrated grade) is 1:(2-5) (w/v);

(b3) admixing the microorganism solution at step (i) into the basic temporary solution at a ratio of (1-2): 10 (w/v) to obtain a foundation temporary solution; and (b4) adjusting pH of the foundation temporary solution reached 6.8-7.2, then fermenting at 30° C.-40° C. for 125-135 hours to obtain the chitin temporary mixture from oyster mushroom;

(B) centrifuging the chitin mixture at a speed of 3500-6500 rpm to separate the residue to obtain a temporary solution; and (C) adding (0.001-0.2) parts of Lactic anhydride into the temporary solution by dropped, adding (0.001-0.8) parts of pyridine solution combined with stirring at 50 rpm for 35 minutes, and adding (0.01-2.5) parts of ethanol solution 75% combined with stirring at 50 rpm for 5 minutes, then stop stirring and let stand for 30 minutes to obtain the modified chitosan ingredient;

in which, prepare the solution containing polysaccharide by mixing a Polysaccharopeptide (PSP) component is extracted from a solution of turkey tail mushroom extract with a first percentage (%) by weight and a Polysaccharide K (PSK) component is extracted from the solution of turkey tail mushroom extract with a second percentage (%) by weight, combining stirring for 10 minutes;

wherein prepare the solution of turkey tail mushroom extract comprising performing in a specific order from (A') to (D'):

(A') fermenting a turkey tail mushroom mixture with the addition of a microorganism preparations in ratio (45-55): 1 at 30° C.-35° C. combined with stirring at 120 rpm for 35-40 hours, and centrifuging at a speed of 6000 rpm for 60 minutes to obtain a first solution and a first residue;

wherein the turkey tail mushroom mixture comprising (1-2) parts a first turkey tail mushroom component with (1-2) parts a second turkey tail mushroom component, (1-2) parts a third turkey tail mushroom component, (1-2) parts a fourth turkey tail mushroom component, and (1-2) parts a fifth turkey tail mushroom component;

the first turkey tail mushroom component is obtained by cultivating Trametes versicolor (L.) Pilat on biomass growth medium;

the second turkey tail mushroom component is obtained by cultivating Trametes versicolor (L.) Lioud (1920) on biomass growth medium;

the third turkey tail mushroom component is obtained by cultivating Trametes sanguinea (L.) Imazeki on biomass growth medium;

the fourth turkey tail mushroom component is obtained by cultivating Trametes versicolor BRG04 on biomass growth medium;

the fifth turkey tail mushroom component is obtained by cultivating Pycnoporus sanguineus (L.: Fr.) Murrill on biomass growth medium;

the biomass growth medium comprising: glucose having 30 g/L, peptone having 4 g/L, magnesium sulfate (MgSO$_4$) having 0.5 g/L, and potassium dihydrogen phosphate (KH$_2$PO$_4$) having 1 g/L;
wherein the microorganism preparations comprising (1-3) parts a first nutrient broth solution with (1-3) parts a second nutrient broth solution, and (1-3) parts a third nutrient broth solution;
the first nutrient broth solution cultivating *Lactobacillus plantarum* (identified on the gene bank as JQ937330.1) on LB medium;
the second nutrient broth solution cultivating *Lactobacillus acidophilus* (identified on the gene bank as OK398226.1) on LB medium; and
the third nutrient broth solution cultivating *Bacillus subtilis* (identified on the gene bank as KY777343.1) on LB medium;
(B') extracting the first residue with water at a ratio of 1:(5-7) at 100° C. for 10-15 minutes to obtain a second solution and a second residue;
(C') extracting the first residue with water at a ratio of 1:(5-7) at 55° C. for 2 hours, then filtering to remove residue, and neutralizing pH to 6.8-7.2 to obtain a third solution; and
(D') mixing the first solution with the second solution, and the third solution to obtain the solution of turkey tail mushroom extract;
the polysaccharopeptide (PSP) component is extracted from the solution of turkey tail mushroom extract comprising performing in a specific order from (a) to (b):
(a) mixing the solution of turkey tail mushroom extract with water at a ratio of 1/32 with stirring at 1000 rpm for 5 minutes, then extracting at 121° C. for 35 minutes, then adding ammonium salt saturated sulfate 80% into said extract at ratio of 1:3 and overnight at 4° C. to form precipitate, and centrifuging at a speed of 8000 rpm for 15 minutes to collect a first precipitate; and
(b) dissolving the first precipitate with water at a ratio of 1:5, then filtering by the membrane filter having a pore size of 30 Kda to collect a fraction that does not pass through the membrane filter, and drying the fraction at 35° C.-42° C. for 35 hours to obtain the the polysaccharopeptide (PSP) component;
wherein prepare the Polysaccharide K (PSK) component from the turkey tail mushroom extract ingredient comprising performing in a specific order from (a') to (b'):
(a') mixing the turkey tail mushroom extract ingredient with water at a ratio of 1/32 with stirring at 1000 rpm for 5 minutes, then extracting at 121° C. for 45 minutes, then adding ethanol solution 60% into said extract at ratio of 1:3 and overnight at 4° C. to form precipitate, and centrifuging at a speed of 8000 rpm for 25 minutes to collect a second precipitate; and
(b') washing the second precipitate by ethanol solution 60%, then drying at 35° C.-42° C. for 28 hours to obtain the Polysaccharide K (PSK) component;
in which, prepare the solution containing dissolving solvent by dissolving water and Tween 80 with a third percentage (%) by weight at 45° C. combining stirring for 15 minutes, then continue to add Dimethyl Sulfoxide (DMSO) solution with a fourth percentage (%) by weight, PEG-400 (Poly Ethylene Glycol-400) with a fifth percentage (%) by weight and hyaluronic acid solution with a sixth percentage (%) by weight, combining with stirring for 20 minutes at 45° C.;
in which, prepare the solution containing nano silver by performing a blend of a solution extracted from plants with a seventh percentage (%) by weight, an aqueous soluble silver salt with a eighth percentage (%) by weight, then treating by ultrasonic with amplitude 25% at 35° C.-42° C. for 10 minutes, and adding an alginate solution 1% with a ninth percentage (%) by weight, and an ascorbic acid solution with a tenth percentage (%) by weight, combined with stirring at 55° C.-60° C. for 20 minutes;
wherein the solution extracted from plants is prepared by sequentially mixing in a container a lotus leaf extract/essential oil, of a grapefruit peels extract/essential oil, a piper seeds extract/essential oil, an *ardisia* leaf extract/essential oil, a *Gomphrena celosioides* Mart. extract/essential oil to form a mixture, and a *Selaginella tamariscina* (Beauv.) Spring extract/essential oil; wherein after each addition of an extract/essential oil the mixture is stirred until the mixture is homogenous;
wherein the piper seeds extract/essential oil is extracted from piper seeds crushed or not crushed, and immersed in solvent, or saturated brine solution; in which piper seeds including *Piper nigrum* L., *Piper bavinum* C. DC., *Piper saxicola* C. DC., *Piper gymnostachyum* C. DC., *Piper brevicaule* C. DC., *Piper pierrei* C. DC, *Piper boehmeriifolium* (Miq.) Wall. ex C. DC., and *Piper retrofractum* Vahl;
wherein the *ardisia* leaf extract/essential oil is extracted from *ardisia* leaf crushed/chopped/or not chopped, and immersed in solvent, or saturated brine solution; in which *ardisia* leaf including *Ardisia balansana* Yang, *Ardisia caudata* Hemsl., *Ardisia incarnata* Pitard, *Ardisia insularis* Mez., *Ardisia maculosa* Mer., *Ardisia primulifolia* Gardn., *Ardisia pseudocrispa* Pit., *Ardisia splendens* Pit., and *Ardisia tsangii* E. Walker;
wherein the aqueous soluble silver salt is selected from the group consisting of silver acetate, silver fluogallate, silver nitrate, and silver sulfate; in which aqueous soluble silver salt has a concentration of 0.02 M;
(ii) mixing the solutions prepared in step (i) in two stages:
a stage 1: creating a homogeneous solution by mixing the prepared solutions in the order that the modified chitosan ingredient, the solution containing polysaccharide, and the solution containing dissolving solvent; wherein after each addition of said ingredient mixed at 28° C.-38° C. with stirring at 500-1000 rpm for 5-20 minutes; and
a stage 2: admixing the solution containing nano silver into the homogeneous solution with combined stirring at 1500 rpm for 5-20 minutes at 28° C.-38° C., to obtain a foundation mixture;
(iii) loading the foundation mixture into a electrospinning device according to predetermined specifications to obtain the antibacterial modified chitosan-based hemostatic material in the form of nanofibers; wherein predetermined specifications including: injection speed 0.8-1.4 mL/h, voltage 12-20 kV, collection distance 8-21 cm, and rolling speed at 30-50 rpm;

wherein the antibacterial modified chitosan-based hemostatic material having rapid hemostasis and antibacterial activities; and
(iv) applying the antibacterial modified chitosan-based hemostatic material to a bleeding tissue on the surface of skin of a subject in need thereof to prevent bleeding and fluid exudation from the tissue, and promoting bacteriostatic and anti-inflammatory effects on the wound surface;
wherein the antibacterial modified chitosan-based hemostatic material containing hydrophilic group, pH is 7.5-8.5, adhesion 35-50 mPas at 36° C.-38° C., and has an in vitro clotting time of less than 50 s for its use to treat a bleeding tissue of animal that forms a modified chitosan-blood coagulation matrix upon contacting the bleeding tissue.

2. The method of claim 1, wherein aqueous soluble silver salt is silver nitrate 0.02M.

3. The method of claim 1, wherein at step (iii) predetermined specifications including: injection speed 1-1.2 mL/h, voltage 15-18 kV, collection distance 10-14 cm, and rolling speed at 40-45 rpm.

4. The method of claim 3, wherein at step (iii) predetermined specifications including: injection speed 1.2 mL/h, voltage 16 kV, collection distance 12 cm, and rolling speed at 45 rpm.

5. The method of claim 1, wherein at step (iii) further comprising, before the loading, dissolving the foundation mixture with a solvent; wherein the solvent includes dimethylacetamide (DMAc), acetone (Ac), acid trifluoroacetic (TFA), acid acetic, acid citric, acid oxalic, acid proprionic, acid ascorbic, acid hydrochloric, acid formic, acid salicylic, acid lactic, dichloromethane (DCM), ethyl acetate (EA), tetrahydrofuran (THF), dimethylformamide (DMF), ethylene chloride, and a combination thereof.

6. The method of claim 1, wherein said rapid hemostasis and antibacterial activities depend on the percentage (%) of the weight of each ingredient, including a first formula, a second formula, a third formula, and a fourth formula; and in which the third formula is stronger than the first formula, the second formula is stronger than the fourth formula and the first formula is stronger than the second formula; in which the comparative factor is rapid hemostasis, and antibacterial activities.

7. The method of claim 6, wherein the first formula comprising:
the polysaccharopeptide (PSP) component having 0.1%-0.4% by weight;
the polysaccharide K (PSK) component having 0.6%-0.9% by weight;
Dimethyl Sulfoxide (DMSO) solution having 0.13%-1.5% by weight;
Tween 80 having 0.008%-0.08% by weight;
PEG-400 (Poly Ethylene Glycol-400) having 0.03%-0.18% by weight;
the hyaluronic acid solution having 0.005%-0.05% by weight;
the solution extracted from plants having 0.1%-0.25% by weight; wherein the solution extracted from plants including: 0.015%-0.075% by weight of the lotus leaf extract/essential oil, 0.012%-0.06% by weight of the grapefruit peels extract/essential oil, 0.005%-0.76% by weight of the piper seeds extract/essential oil, 0.082%-0.045% by weight of the *ardisia* leaf extract/essential oil, 0.001%-0.05% by weight of the *Gomphrena celosioides* Mart. extract/essential oil, and 0.003%-0.084% by weight of the *Selaginella tamariscina* (Beauv.) Spring extract/essential oil;
the aqueous soluble silver salt having 0.08%-0.27% by weight;
the alginate ingredient 1% having 0.3%-0.65% by weight;
the ascorbic acid solution having 0.001%-0.005% by weight;
the modified chitosan ingredient having 50%-85% by weight; and
the remainder is the water.

8. The method of claim 6, wherein the second formula comprising:
the polysaccharopeptide (PSP) component having 0.6%-0.9% by weight;
the polysaccharide K (PSK) component having 0.1%-0.4% by weight;
Dimethyl Sulfoxide (DMSO) solution having 0.13%-1.5% by weight;
Tween 80 having 0.008%-0.08% by weight;
PEG-400 (Poly Ethylene Glycol-400) having 0.03%-0.18% by weight;
the hyaluronic acid solution having 0.005%-0.05% by weight;
the solution extracted from plants having 0.1%-0.25% by weight; wherein the solution extracted from plants including: 0.015%-0.075% by weight of the lotus leaf extract/essential oil, 0.012%-0.06% by weight of the grapefruit peels extract/essential oil, 0.005%-0.76% by weight of the piper seeds extract/essential oil, 0.082%-0.045% by weight of the *ardisia* leaf extract/essential oil, 0.001%-0.05% by weight of the *Gomphrena celosioides* Mart. extract/essential oil, and 0.003%-0.084% by weight of the *Selaginella tamariscina* (Beauv.) Spring extract/essential oil;
the aqueous soluble silver salt having 0.08%-0.27% by weight;
the alginate ingredient 1% having 0.3%-0.65% by weight;
the ascorbic acid solution having 0.001%-0.005% by weight;
the modified chitosan ingredient having 50%-85% by weight; and
the remainder is the water.

9. The method of claim 6, wherein the third formula comprising:
the polysaccharopeptide (PSP) component having 0.1%-0.5% by weight;
the polysaccharide K (PSK) component having 0.1%-0.5% by weight;
Dimethyl Sulfoxide (DMSO) solution having 0.13%-1.5% by weight;
Tween 80 having 0.008%-0.08% by weight;
PEG-400 (Poly Ethylene Glycol-400) having 0.03%-0.18% by weight;
the hyaluronic acid solution having 0.005%-0.05% by weight;
the solution extracted from plants having 0.1%-0.25% by weight; wherein the solution extracted from plants including: 0.015%-0.075% by weight of the lotus leaf extract/essential oil, 0.012%-0.06% by weight of the grapefruit peels extract/essential oil, 0.005%-0.76% by weight of the piper seeds extract/essential oil, 0.082%-0.045% by weight of the *ardisia* leaf extract/essential oil, 0.001%-0.05% by weight of the *Gomphrena celosioides* Mart. extract/essential oil, and 0.003%-0.084% by weight of the *Selaginella tamariscina* (Beauv.) Spring extract/essential oil;

the aqueous soluble silver salt having 0.08%-0.27% by weight;

the alginate ingredient 1% having 0.3%-0.65% by weight;

the ascorbic acid solution having 0.001%-0.005% by weight;

the modified chitosan ingredient having 50%-85% by weight; and the remainder is the water.

10. The method of claim 6, wherein the fourth formula comprising:

the polysaccharopeptide (PSP) component having 0.6%-0.9% by weight;

the polysaccharide K (PSK) component having 0.6%-0.9% by weight;

Dimethyl Sulfoxide (DMSO) solution having 0.13%-1.5% by weight;

Tween 80 having 0.008%-0.08% by weight;

PEG-400 (Poly Ethylene Glycol-400) having 0.03%-0.18% by weight;

the hyaluronic acid solution having 0.005%-0.05% by weight;

the solution extracted from plants having 0.1%-0.25% by weight; wherein the solution extracted from plants including: 0.015%-0.075% by weight of the lotus leaf extract/essential oil, 0.012%-0.06% by weight of the grapefruit peels extract/essential oil, 0.005%-0.76% by weight of the piper seeds extract/essential oil, 0.082%-0.045% by weight of the *ardisia* leaf extract/essential oil, 0.001%-0.05% by weight of the *Gomphrena celosioides* Mart. extract/essential oil, and 0.003%-0.084% by weight of the *Selaginella tamariscina* (Beauv.) Spring extract/essential oil;

the aqueous soluble silver salt having 0.08%-0.27% by weight;

the alginate ingredient 1% having 0.3%-0.65% by weight;

the ascorbic acid solution having 0.001%-0.005% by weight;

the modified chitosan ingredient having 50%-85% by weight; and the remainder is the water.

11. The method of claim 1, wherein the bleeding tissue of the subject is selected from the group consisting of mammals, birds, and reptiles.

12. The method of claim 11, wherein the bleeding tissue of mammals is human.

13. The method of claim 1, wherein at step (C) adding (0.01-0.1) parts of Lactic anhydride into the temporary solution by dropped.

14. The method of claim 1, wherein at step (C) adding (0.01-0.5) parts of pyridine solution.

* * * * *